United States Patent [19]

Nakazato

[11] Patent Number: 5,298,140
[45] Date of Patent: Mar. 29, 1994

[54] REACTION APPARATUS FOR BIOCHEMICAL EXAMINATION

[75] Inventor: Tokiya Nakazato, Urawa, Japan

[73] Assignee: Helena Laboratories Co., Ltd., Japan

[21] Appl. No.: 942,180

[22] Filed: Sep. 9, 1992

[30] Foreign Application Priority Data

Sep. 13, 1991 [JP] Japan .................. 3-235024

[51] Int. Cl.⁵ .................................................. C25B 9/00
[52] U.S. Cl. .................................................. 204/299 R
[58] Field of Search ................................... 204/299 R

[56] References Cited

U.S. PATENT DOCUMENTS

| Re. 28,339 | 2/1975 | Maxon | 23/230 R |
|---|---|---|---|
| 3,139,810 | 7/1964 | Tobin, Jr. | 95/89 |
| 3,675,488 | 7/1972 | Viktora et al. | 73/421 R |
| 3,896,021 | 7/1975 | Fosslien | 204/299 R |
| 3,918,910 | 11/1975 | Soya et al. | 23/263 R |
| 4,059,501 | 11/1977 | Strickler | 204/299 R |

FOREIGN PATENT DOCUMENTS

| 0304921 | 3/1989 | European Pat. Off. . |
|---|---|---|
| 0312034 | 4/1989 | European Pat. Off. . |
| 0484864 | 5/1992 | European Pat. Off. . |
| 2214127 | 8/1974 | France . |
| 1-101453 | 4/1989 | Japan . |

Primary Examiner—John Niebling, Cybille Delacroix-Muirheid assistant
Attorney, Agent, or Firm—Spencer, Frank & Schneider

[57] ABSTRACT

A reaction apparatus for a biochemical examination is provided having at least a pair of band-shaped conveying members, a portion of each of which proceeds over a predetermined distance in the same direction in a closely contacted state, and which convey a sample-supporting thin film while sandwiching it between the closely contacted portions, and a heat source which is provided in the vicinity of the closely contacted portions of the pair of band-shaped conveying members, and which maintains at a predetermined temperature the sample-supporting thin film sandwiched between the closely contacted portions. The sample-supporting thin film is conveyed from one side to the other side between the pair of band-shaped conveying members. On the other side, the sample-supporting thin film is supplied with the reagent, then caused to approach the heat source while being sandwiched between the band-shaped conveying members. By means of the heat source, the sample-supporting thin film is maintained at a predetermined temperature, whereby the reaction between the sample and the reagent is promoted.

7 Claims, 7 Drawing Sheets

REACTION APPARATUS FOR BIOCHEMICAL EXAMINATION

BACKGROUND OF THE INVENTION

1. Field of the Invention

The present invention relates to a reaction apparatus for a biochemical examination, designed to supply a reagent appropriately to a support medium such as cellulose acetate film, agarose, agar, or polyacrylamide gel, in an electrophoresis method for biochemical examinations and researches in which a sample for analysis, such as serum protein, isozyme or lipoprotein, is caused to migrate through the support medium, a reagent is reacted with the sample, and the resulting substance is measured.

2. Description of the Prior Art

Figure 1:
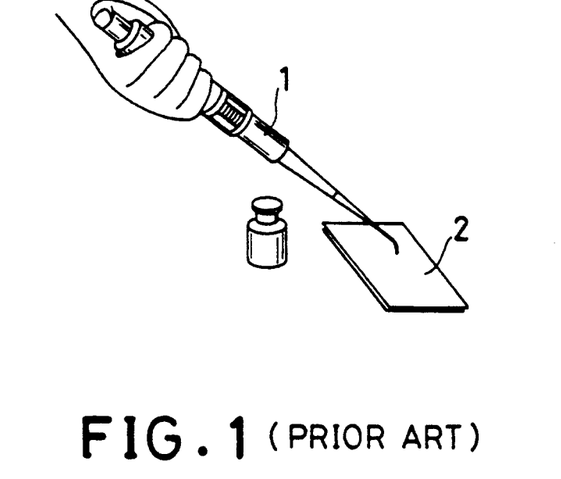
FIG. 1 is a perspective view illustrating a conventional method of supplying a reagent to a support medium which has been electrophoresed.
Figure 2:
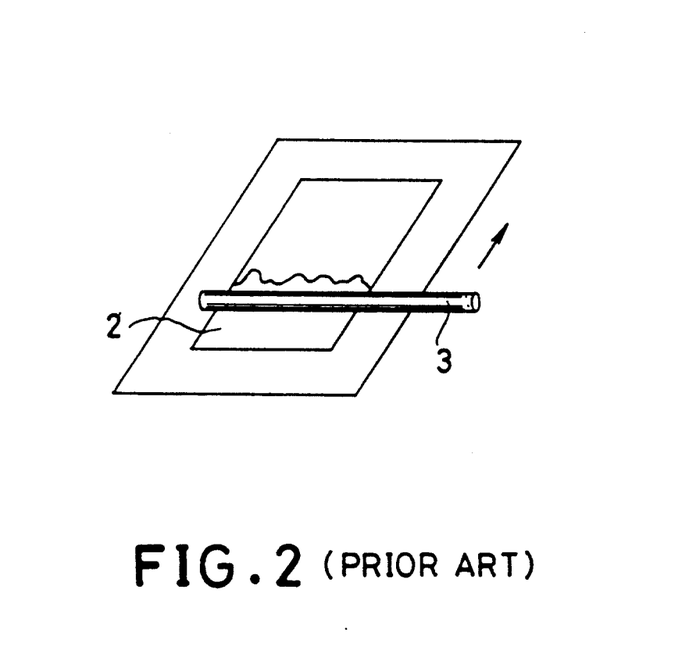
FIG. 2 is a perspective view illustrating the conventional method of supplying a reagent to a support medium which has been electrophoresed.

In the past, the supply of a reagent to a support medium in the above-mentioned electrophoresis method was performed in the following two manners:

The first method is to supply, by means of, say, a pipette 1, drops of a reagent dissolved before use to the entire surface of an electrophoresed support medium 2, as shown in FIG. 1, allow this reagent to be absorbed to the support medium 2 for a certain period of time, and then remove the excess reagent by applying a glass rod 3 or the like, as shown in FIG. 2.

Figure 3:
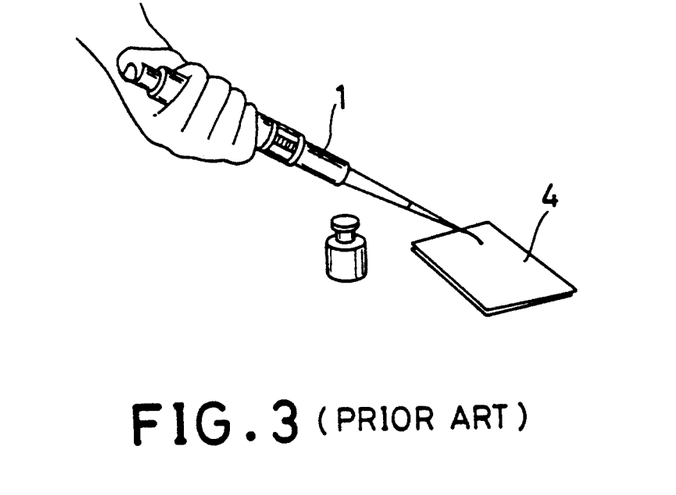
FIG. 3 is a perspective view illustrating another conventional method of supplying a reagent to a support medium which has been electrophoresed.
Figure 4:
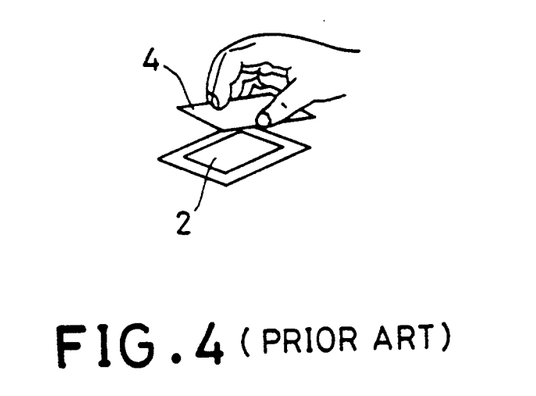
FIG. 4 is a perspective view illustrating the another conventional method of supplying a reagent to a support medium which has been electrophoresed.
Figure 5:
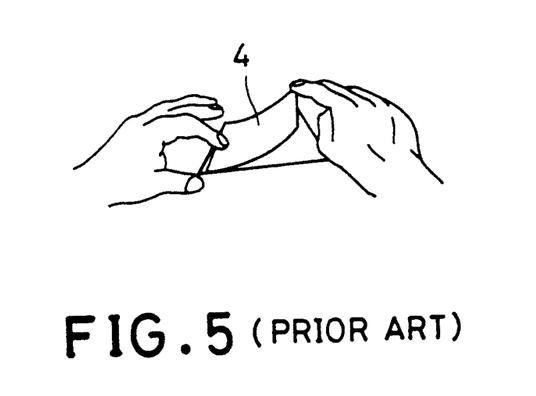
FIG. 5 is a perspective view illustrating the another conventional method of supplying a reagent to a support medium which has been electrophoresed.

The second method is to supply, by means of, say, a pipette 1, drops of a reagent dissolved before use to an impregnation membrane 4 such as a filter paper or cellulose acetate membrane, as shown in FIG. 3, allow the reagent to be absorbed thereto, and bring this reagent-impregnated membrane 4 into close contact with an electrophoresed support medium 2, as shown in FIGS. 4 and 5.

After the reagent has been absorbed to the support medium, the reaction is performed in an incubator.

With the method of supplying drops of the reagent to the entire surface of the support medium as illustrated in FIGS. 1 and 2, however, it is difficult to absorb a predetermined amount of the reagent to the support medium with good reproducibility, and a high grade of operating skill is required, thus resulting in a poor efficiency. With this method, moreover, the sample tends to solve out from the support medium when the excess reagent on the support medium is removed. Once it has solved out, the resulting reaction patterns may blur at the contour, or overlap neighboring patterns, making assay often impossible.

With the method of closely contacting the reagent-impregnated membrane with the support medium as shown in FIGS. 3, 4 and 5, on the other hand, it is difficult to absorb the reagent from the impregnated membrane to the support medium with good reproducibility, and the procedure involved is complicated. Furthermore, the reaction product formed in the support medium may move to the impregnation membrane, impairing the clarity of reaction patterns.

SUMMARY OF THE INVENTION

This invention is characterized by a reaction apparatus for a biochemical examination, at least comprising:

a pair of band-shaped conveying members, a portion of each of which proceeds over a predetermined distance in the same direction in a closely contacted state, and which convey a sample-supporting thin film while sandwiching it between the closely contacted portions, and a heat source which is provided in the vicinity of the closely contacted portions of the pair of band-shaped conveying members, and which maintains at a predetermined temperature the sample-supporting thin film sandwiched between the closely contacted portions.

In this invention, a pair of rollers are used to form the closely contacted portions of the band-shaped conveying members.

This invention also permits a construction in which the pair of band-shaped conveying members are adapted to be capable of moving in normal and reverse directions, a reagent introduction portion for introducing a thin layer reagent supplier having a reagent coated onto the surface of a thin film substrate is connected to one end of the pair of band-shaped conveying members, and an introduction port for the sample-supporting thin film is formed at the other end of the pair of band-shaped conveying members.

In this construction, it is desirable that a reagent cartridge capable of introducing one by one a multiplicity of thin layer reagent suppliers placed in a container is detachably mounted to the reagent introduction portion.

In the present invention, a construction is also possible in which the pair of band-shaped conveying members are constructed of a plastic film, a horizontal conveying portion of the band-shaped conveying members situated at a lower position of the pair of band-shaped conveying members is formed so as to be longer toward the introduction port than a horizontal conveying portion of the upper band-shaped conveying members in close contact with the former horizontal conveying portion, and a reagent dropping device for dropping a liquid reagent onto the surface of the sample-supporting this film moving on the extended portion is provided above the extended portion.

Another construction may also be permitted in which the pair of band-shaped conveying members are constructed of a plastic film, and a reagent is coated onto that surface of one of the band-shaped conveying members which comes into close contact with the sample-supporting thin film.

According to the reaction apparatus for a biochemical examination of the above construction in accordance with the present invention, the reagent can be supplied uniformly and automatically into the (electrophoresed) support medium, and the sample-supporting member can be placed at a stable reaction temperature, thus making it possible to perform biochemical examinations rapidly and with good reproducibility.

The above and other objects, effects, features and advantages of the present invention will become more apparent from the following description of embodiments there of taken in conjunction with the accompanying drawings.

DETAILED DESCRIPTION OF PREFERRED EMBODIMENTS

Embodiment 1

A preferred thin layer reagent supplier for use in the apparatus of this invention will be described first.

Figure 6:
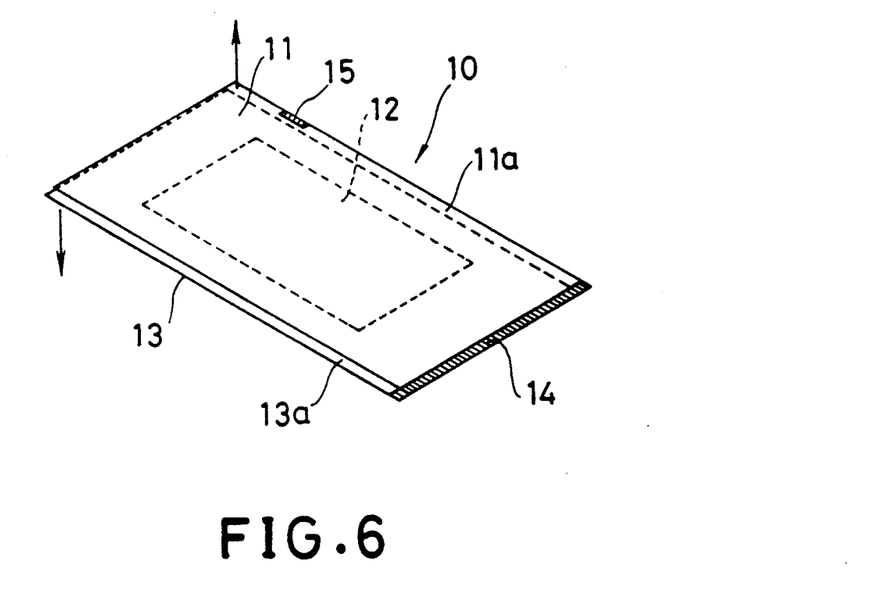
FIG. 6 is a perspective view of a preferred thin layer reagent supplier for use in the present invention.

The thin layer reagent supplier is a special reagent supplier comprising a thin film such as a polyester film onto which a reagent has been coated and dried. As shown in FIG. 6, a thin layer reagent supplier 10 as illustrated here is prepared in the following manner: A reagent-containing agent 12 is adhered to the center of the upper surface of a thin layer substrate (polyester film) 11, whereafter the agent is dried. Then, the substrate 11 is cut into a single strip, and a cover (e.g. a polyester film 38 $\mu$m in thickness) 13 is attached on the coated surface side of the thin layer reagent supplier by heat-sealing at an end 14 thereof (hereinafter referred to as the heat-seal portion). At this time, it is preferred that the cover 13 be slightly displaced from the substrate 11 (e.g. by 10 mm) to form a peel margin 11a and a peel margin 13a in the thin layer substrate 11 and the cover 13, respectively, for easy separation of the cover 13.

Provision of the cover 13 can prevent the drying and surface contamination of the reagent-containing agent 12 during its reaction. It can also improve close contact of the reagent with the support medium, and prevent contamination of the surrounding devices during close contact.

The numeral 15 in FIG. 6 is a stop-mark.

Figure 7:
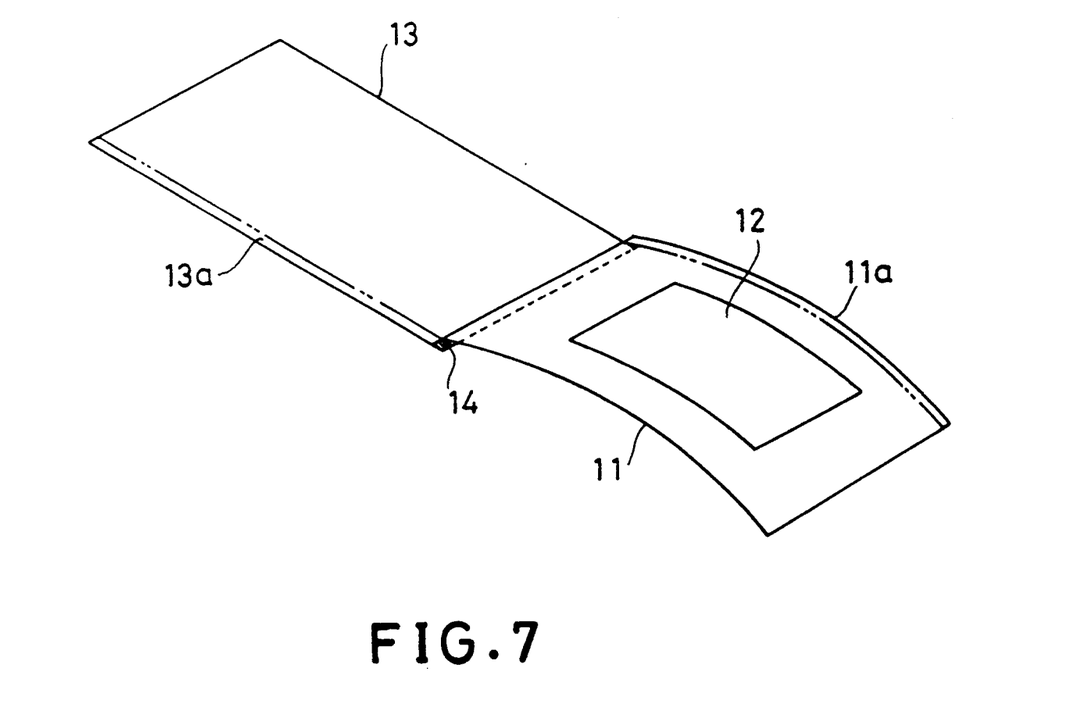
FIG. 7 is a perspective view showing a state in which the cover of the thin layer reagent supplier has been peeled off.

FIG. 7 shows a state of the thin layer reagent supplier 10 in which the peel margin 11a of the thin layer substrate 11 and the peel margin 13a of the cover 13 are engaged separately, and pulled in opposite directions (arrows in FIG. 6), thereby opening the cover 13 and exposing the reagent-containing agent 12.

Figure 8:
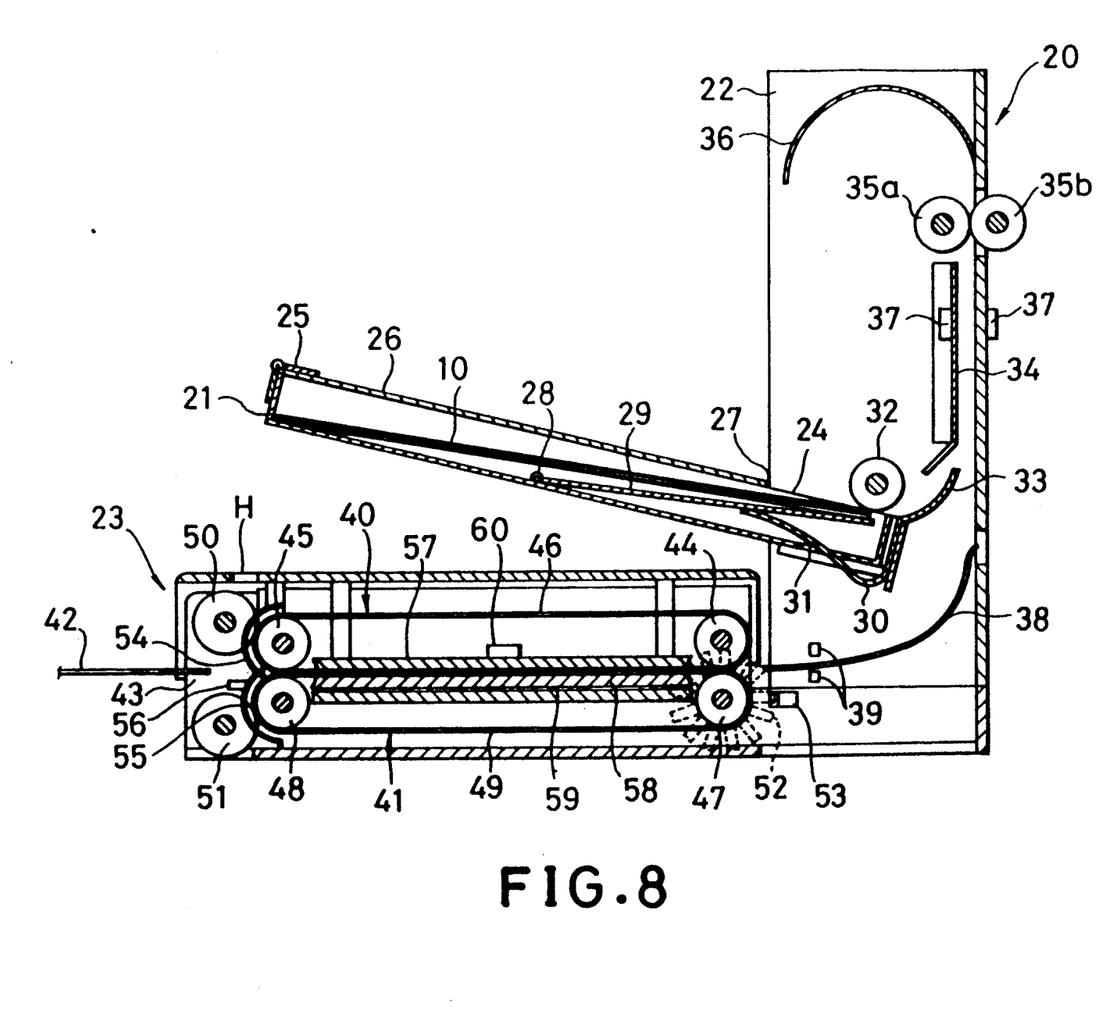
FIG. 8 is a side sectional view showing a first embodiment of the apparatus in accordance with the present invention.

FIG. 8 is a sectional block diagram showing an embodiment of the apparatus in accordance with this invention. This apparatus is composed of a body 20, and a reagent cartridge 21 which houses a multiplicity of thin layer reagent suppliers 10 therein, and which supplies the thin layer reagent suppliers 10 successively into the body 22.

The body 20 is L-shaped when viewed sideways, and comprises a reagent introduction portion at a vertical position and a reaction portion 23 at a horizontal position.

Below the center of the front surface of the reagent introduction portion 22 (leftward of the drawing) is formed a mounting port 24 for mounting the reagent cartridge 21.

Prior to explanation for the inside structure of the body 22, the structure of the reagent cartridge 21 will be described for convenience's sake.

The reagent cartridge 21 is a shallow-bottomed box-shaped container, provided at its upper surface with a cover 26 which is openable and closable about a hinge 25 so as to facilitate accommodation of the thin layer reagent supplier 10 from above. The cover 26 is not large enough to cover the entire upper surface of the cartridge 21, but is formed to be somewhat shorter so that a supply port 27 to the body 20 can be secured. On the inside bottom surface of the cartridge 21 is mounted a push-up plate 29 supported pivotally by a hinge 28 approximately at the center. The forward end of the push-up plate 29 is situated in the supply port 27. At the bottom surface of the insertion forward end portion of the cartridge 21 is formed an insertion port 31 for a push-up spring 30 provided deep behind the insertion port 24 of the reagent introduction portion 22. The accommodation of the thin layer reagent supplier 10 into the cartridge 21 of such a structure is carried out in such a manner that the heat-seal portion 14 of the reagent supplier 10 is positioned in the supply port 27.

Here, a description of the inner structure of the body 20 will be offered.

As described earlier, the push-up spring 30 is fixed deep behind the mounting port 24 of the reagent introduction portion 22, and a take-off roller 32 with a built-in one-way clutch is attached at an upper part deep behind the mounting port 24. When the cartridge 21 is mounted into the mounting port 24 of such a structure, the push-up plate 29 is pushed up by the spring 30, whereby the front end portion (heat-seal portion) of the thin layer reagent supplier 10 within the cartridge 21 is brought into contact with the take-off roller 32. Therefore, the rotation of the take-off roller 32 results in the withdrawal of the thin layer reagent supplier 10 within the cartridge 21 into the reagent introduction portion 22. Beside and above the take-off roller 32 are attached guide plates 33 and 34, respectively. Further above them are provided a pair of rollers 35a, 35b capable of making normal and reverse rotations so as to guide the reagent supplier 10 withdrawn by the roller 32 upwards transiently. Further above the rollers 35a, 35b is disposed a curved guide plate 36 so that the reagent supplier 10 sent upwards will be curved in an attempt to reduce the volume occupied by the reagent introduction portion 22. Near the center of the guide plate 34 is installed a detector 37 which detects the stop-mark of the reagent supplier 10. When the stop-mark is detected by the detector 37, the end portion of the reagent supplier 10 (the portion opposite to the heat-seal portion) is adapted to have passed the guide plate 33 completely by properly setting the printing position of the stopmark 15 (FIG. 6) on the reagent supplier 10 and the installing position of the detector 37. When the detector 37 detects the stop-mark of the reagent supplier 10 being conveyed upwards, the rollers 35a, 35b revolve reversely upon receipt of an instruction from the controlling portion of this apparatus (not shown), conveying the reagent supplier 10 downwards. At this time, belt conveyors 40, 41 begin rotation so that they can convey the reagent supplier 10 toward the introduction port 43. Afterwards, the conveyed front end of the reagent supplier 10 is an openable and closable end opposite to the heat-seal portion. At a bottom portion of the reagent introduction portion 22 is attached an inclined guide plate 38 to guide the reagent supplier 10 to the reaction portion 23. At a front end portion of the guide plate 38 facing the reaction portion 23 is installed a detector 39 which detects the stop-mark on the reagent supplier 10.

In the reaction region 23 are provided an upper belt conveyor 40 and a lower belt conveyor 41 which act cooperatively as a pair. One end of this pair of belt conveyors 40, 41 is adjacent to the guide plate 38, while the other end thereof is adjacent to the introduction port 43 of an electrophoresis support medium (sample-supporting thin film) 42 to be described later. The upper belt conveyor 40 is composed of a pair of pulleys 44, 45 and a belt (band-shaped conveying member) 46 which is caused to make revolutions by these pulleys 44, 45. These pulleys 44, 45 are constructed such that one or both of them is or are driven in normal and reverse directions by a drive source (not shown). Similarly, the lower belt conveyor 41 is composed of pulleys 47, 48 and a belt (band-shaped conveying member) 49. An end of these belt conveyors 40, 41 on the introduction port 43 side is in contact with corrective rollers 50, 51 for maintaining the speed constant. At the roller 47 are fixed a plurality of choppers 52 for detecting the amount of rotation which are arranged at equal intervals along the periphery of the roller 47. Close to the pulley 47 is disposed a chopper detector 53 which detects each chopper 52.

When the detector 39 detects the stop-mark 15 of the reagent supplier 10, the detector 53 begins to count the number of passages of the choppers 52 rotating at the same time that the belt conveyors 40, 41 begin to rotate. It has been programmed that the controlling device which has received signals of measured values from the detector 53 rotates the belt conveyors 40, 41 until the reagent supplier 10 fully opens (the cover 13 is peeled) as will be described, and then stops these belt conveyors.

Figure 9:
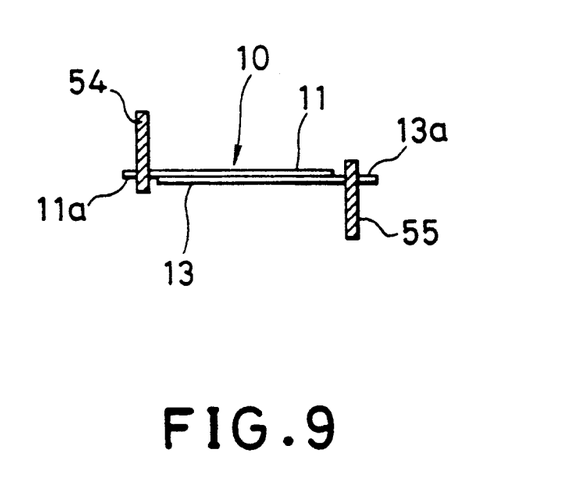
FIG. 9 is a partial front view showing the effect of the small separating plate on the thin layer reagent supplier in the apparatus as the first embodiment.
Figure 10:
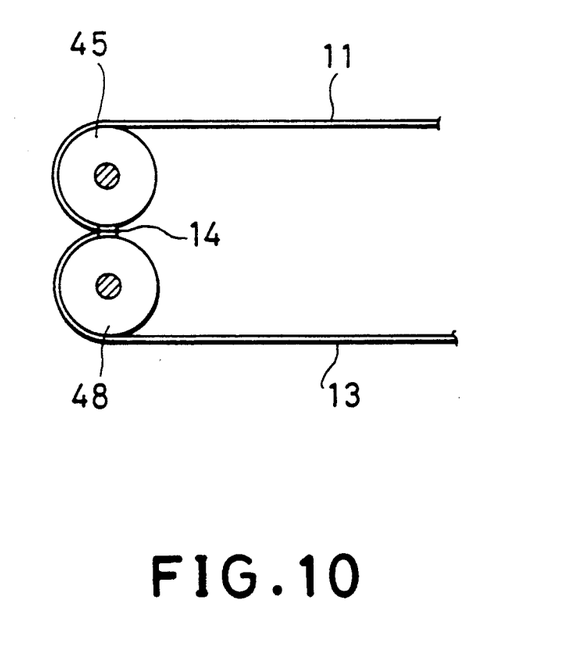
FIG. 10 is a partial side sectional view showing a state of peeling of the thin layer reagent supplier in the first embodiment apparatus.

In the vicinity of the pulleys 45, 48 on the introduction port 43 side are provided small separating plates 54, 55. These small separating plates 54, 55 are members for opening the thin layer reagent supplier 10 that has been conveyed, as illustrated in FIG. 9. The small separating plate 54 engages the peel margin 11a of the reagent supplier 10, while the small separating plate 55 engages the peel margin 13a. When the reagent supplier 10 is advanced in this condition, the thin layer substrate 11 with the peel margin 11a is moved upwards along the small separating plate 54, whereas the cover 13 with the peel margin 13a is moved downwards along the small separating plate 55. Hence, the reagent supplier 10 will have its cover 13 peeled automatically in accordance with the conveyance. As shown in FIG. 10, once the reagent supplier 10 is fully opened, the belt conveyors 40, 41 are stopped by the controlling device (not shown) as already described.

As shown in FIG. 10, the time when the reagent supplier 10 has been fully opened is when preparations have been made for the present apparatus to accept the electrophoresis medium 42. Immediately, the electrophoresis support medium 42 begins to be delivered by the controlling device into the reaction portion 23 of the present apparatus through the introduction port 43. An electrophoresis support medium detector 56 is installed near the pulleys 45, 48 for detecting the arrival of the electrophoresis support medium 42 at a preferred position where it will be sandwiched between the reagent supplier 10.

When the detector 56 has detected the arrival of the electrophoresis support medium 42 at a suitable position for its joining with the reagent supplier 10, the belt conveyors 40, 41 begin to be rotated in an opposite direction to the aforementioned direction, with the progress of the electrophoresis support medium 42 being continued. Then, the reagent supplier 10 is conveyed to a central position of the belt conveyors 40, 41, while sandwiching the electrophoresis support medium 42 between its thin layer substrate 11 and its cover 13. At a time when the electrophoresis support medium 42 is completely sandwiched therebetween, the belt conveyors 40, 41 are stopped. Motion control during this period is performed by the choppers 52, the detectors 53, and the controlling device (not shown). In order to carry out the sandwiching of the electrophoresis support medium 42 by the reagent supplier in a fully closely contacted state, the belts 46, 49 are provided with support plates 57, 58 for ensuring a close contact. By means of these support plates 57, 58, the belts 46, 49 are adapted to move simultaneously in normal and reverse directions in a closely contacted state. Therefore, the reagent supplier 10 and the electrophoresis support medium 42 sandwiched between these belts 46, 49 are in fully close contact.

A heater 59 for promoting the reaction of the electrophoresis support medium 42 which has come into close contact with the reagent supplier 11 to receive the supply of the reagent is mounted to the support plate 58. Thus, the electrophoresis support medium 42 supplied with the reagent in the above manner is heated in a state of close contact with the reagent so that examinations using the reagent can be completed accurately and rapidly. In the drawing, the numeral 60 is a temperature controller for the heater 59.

In Embodiment 1, the body 20 is an L-shaped member comprising the reagent introduction portion 22 arranged at a vertical position in combination with the reaction portion 23 disposed at a horizontal position. This configuration is intended to minimize the area occupied by the apparatus when installed. If the area for installation of the apparatus is ample enough, it will be permissible to dispose the reagent introduction portion at a horizontal position with respect to the reaction portion laid at a horizontal position and to insert the reagent cartridge in a horizontal direction. In this case, the reagent introduction portion requires no reverse mechanism, because the reagent supplier may be conveyed in only one direction. Attendant thereon, the way in which the reagent supplier is set within the cartridge is such that its heat-seal portion will be located deep therein.

In Embodiment 1, it is allowable to use a film not coated with the reagent as the reagent supplier, and to pipette a liquid reagent through a hole H provided in the upper wall between the pulley 45 and the roller 50 as shown in FIG. 8. This system enables the use of a liquid reagent.

In Embodiment 1, it will become possible to charge reagents for respective test parameters, if the mounting port for the cartridge is made into a multi-orifice type as used in an ordinary paper copying machine.

Embodiment 2

Figure 11:
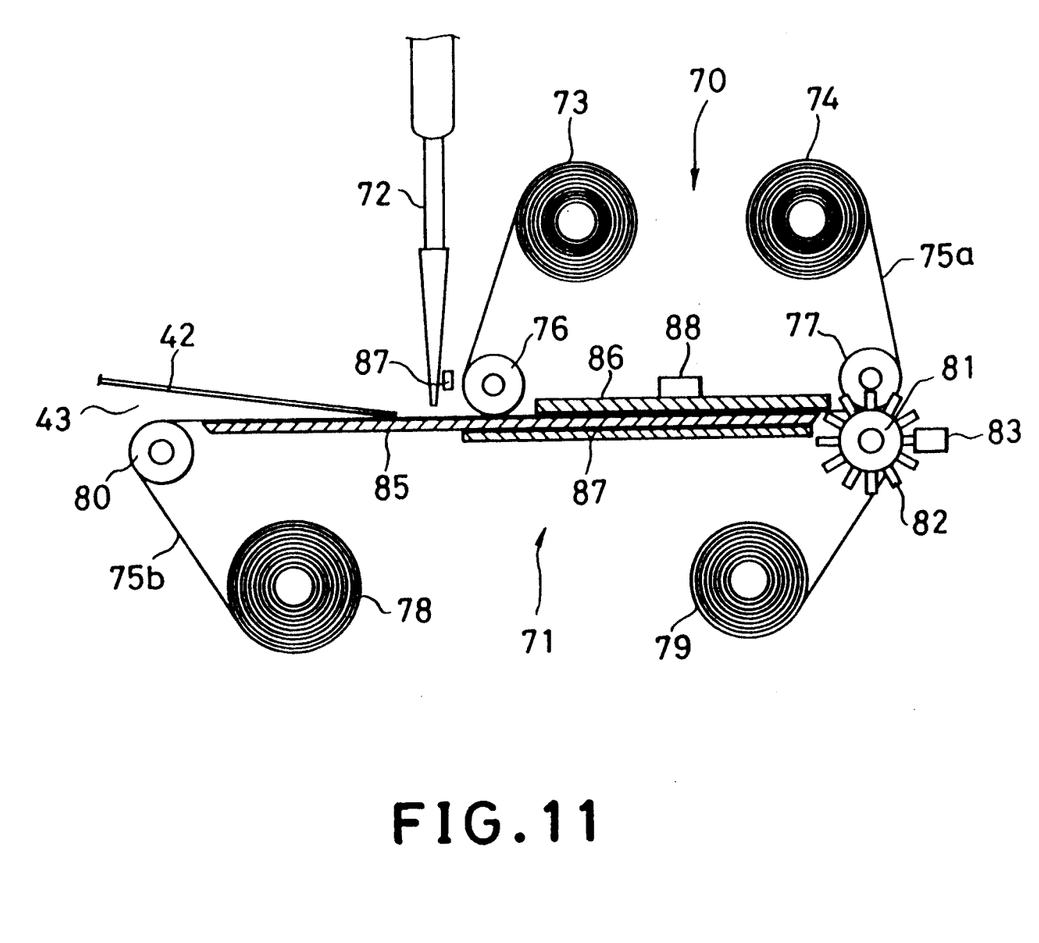
FIG. 11 is a side sectional view showing a second embodiment of the apparatus in accordance with the present invention.

FIG. 11 shows a second embodiment of the apparatus in accordance with the present invention. The apparatus of this embodiment is preferred mainly for a liquid reagent. Instead of a pair of belt conveyors as used in the apparatus of Embodiment 1, the apparatus of this embodiment is provided with a pair of unidirectional conveying devices 70, 71 which comprise a thin film feed roller wrapped with a thin film material (polyester film), and a take-up roller for taking up the thin film material from the feed roller. In this apparatus, the reagent is supplied using a pipette 72. Therefore, no reagent introduction portion is required.

The upper unidirectional conveying device 70 of the above pair of unidirectional conveying devices has a thin film feed roller 73 and a take-up roller 74 as described above. It is also provided with drive rollers 76, 77 for moving a film (band-shaped conveying member) 75a, stretched between the thin film feed roller 73 and the take-up roller 74, horizontally by a predetermined distance.

Similarly, the lower unidirectional conveying device 71 has a thin film feed roller 78, a take-up roller 79, and drive rollers 80, 81, the drive roller 81 being provided with controlling choppers 82. Close to the drive roller 81 is installed a chopper detector 83. The distance between the drive rollers 80 and 81 of the lower conveying device 71 has been set to be much larger, toward the introduction port 43 of the conveying device (left-hand side of the drawing), than the distance between the drive rollers 76 and 77 of the upper conveying device 70. This extension is where the electrophoresis support medium 42 is fed and laid. Above a part of this extension nearer the upper conveying device 70 is disposed the pipette 72. Between the pipette 72 and the drive roller 76 is disposed a detector 84 which detects the electrophoresis support medium 42. Between the drive rollers 80 and 81 of the lower conveying device 71 is provided a support plate 85 for maintaining a horizontal plane of the film (band-shaped conveying member) 75b without allowing the film to sag. Between the drive rollers 76 and 77 of the upper conveying device 70, on the other hand, a press plate 86 is provided so that the upper film and the lower film can move in a closely contacted state. That portion of the support plate 85 which is between the drive rollers 76 and 77 is provided with a heater 87 for promoting the reaction. The numeral 88 denotes a temperature controller for the heater 87.

In the apparatus of the above construction, when the electrophoresed support medium 42 is placed on the film 75b in motion, it is moved to below the pipette 72 by means of the film 75b. When the detector 84 detects the electrophoresis support medium 42, a predetermined amount of reagent is dropped onto the moving support medium 42 from the pipette 72 by the action of a controlling device (not shown). The reagent dropped onto the support medium 42 spreads itself, and is extended by the roller 76, and develops over the entire surface of the support medium 42. When the whole of the support medium 42 is sandwiched between the films 75a and 75b (situated between the rollers 76 and 77), the progress of the film is stopped. Positional control at this time is carried out by the choppers 82, the detector 83, and the controlling device (not shown).

It is permissible, in this case, to provide a step in which the support medium 42 having the reagent coated and spread over its entire surface and being positioned between the rollers 76 and 77 is ejected to a front end portion of the support plate 85 on the introduction port 43 side, and is allowed to stand there for a certain period of time. This step is preferred, because it will make the absorption of the reagent sure.

When the support medium 42 so supplied with the reagent is stopped on the heater 87, heating starts, and the reaction on the support medium 42 proceeds. Upon completion of the reaction, the upper and lower films 75a and 75b are wound round the take-up rollers 74 and 79, respectively, thus discharging the support medium 42 after reaction from the apparatus automatically.

If the reagent is applied beforehand to the surface of the film 75a wound around the upper thin film roller 73, the electrophoresis support medium 42 can be supplied with the reagent without the pipette 72 required.

Embodiment 3

Figure 12:
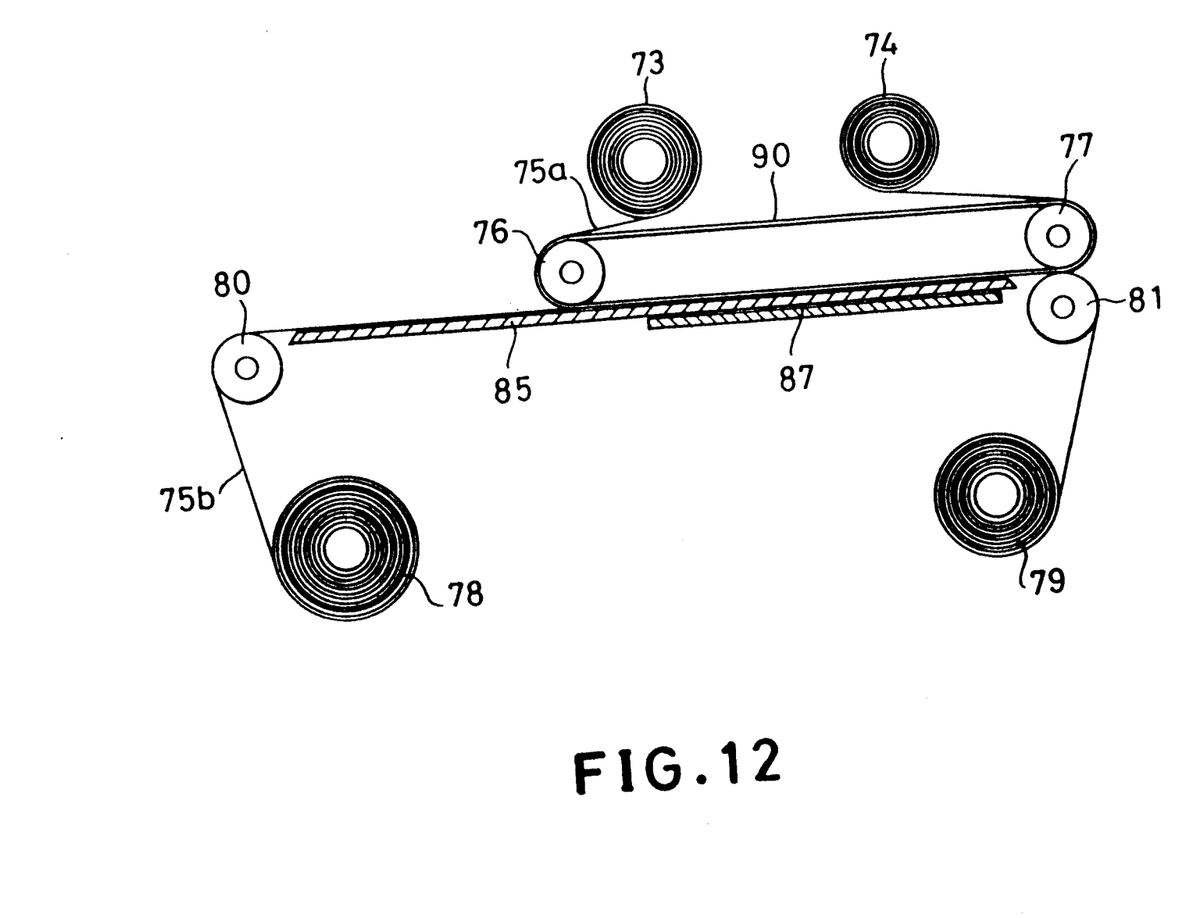
FIG. 12 is a side sectional view showing a third embodiment of the apparatus in accordance with the present invention.

FIG. 12 shows a third embodiment of the apparatus in accordance with the present invention. Since its basic construction is the same as that of Embodiment 2, the same constituent elements will be given the same reference numerals for simplified explanation. The apparatus disclosed herein is characterized by a belt 90 applied between the upper drive rollers 76 and 77. This belt 90 enables the upper film 75a to be fully closely contacted with the lower film 75b on the support plate 85. The presence of the belt 90 also provides the advantage that the movement of the film 75a becomes smooth and uniform.

In the apparatuses of Embodiments 2 and 3, the band-shaped conveying member was composed of a plastic film and was adapted to be wound in a single direction from the thin film feed roller to the take-up roller. This construction was needed for disposable use of the film onto which the reagent was dropped or which was precoated with the reagent.

The combination of the detector and the choppers used in each of the embodiments can be replaced by a stepping motor.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A reaction apparatus for a biochemical examination at least comprising:
   a pair of band-shaped conveying members, a portion of each of which proceeds over a predetermined distance in the same direction in a closely contacted state, and which convey an electrophoresed sample-supporting thin film while sandwiching said sample-supporting thin film between said closely supported contacted portions; and
   a heat source which is provided in the vicinity of said closely contacted portions of said pair of band-shaped conveying members, and which maintains at a predetermined temperature said sample-supporting thin film sandwiched between said closely contacted portions.

2. A reaction apparatus as claimed in claim 1, wherein a pair of rollers are used to form said closely contacted portions of said band-shaped conveying members.

3. A reaction apparatus as claimed in claim 1, wherein said part of band-shaped conveying members are adapted to be capable of moving in normal and reverse directions, a reagent introduction portion for introducing a thin layer reagent supplier having a reagent for standing coated onto the surface of a thin film substrate is connected to one end of said pair of band-shaped conveying members, and an introduction port for said sample-supporting thin film is formed at the other end of said pair of band-shaped conveying members.

4. A reaction apparatus as claimed in claim 3, wherein a reagent cartridge capable of introducing one by one a multiplicity of thin layer reagent suppliers placed in a container is detachably mounted to said reagent introduction portion.

5. A reaction apparatus as claimed in claim 1, wherein said pair of band-shaped conveying members are constructed of a plastic film, a horizontal conveying portion of the band-shaped conveying members situated at a lower position of said pair of band-shaped conveying members is formed so as to be longer toward said introduction port than a horizontal conveying portion of the upper band-shaped conveying member in close contact the said former horizontal conveying portion, and a reagent dropping device for dropping a liquid reagent for staining onto the surface of said sample-supporting thin film moving on said extended portion is provided above said extended portion.

6. A reaction apparatus as claimed in claim 1, wherein said pair of band-shaped conveying members are constructed of a plastic film, and a reagent for staining is coated onto that surface of one of said band-shaped conveying members which comes into close contact with said sample-supporting thin film.

7. A reaction apparatus as claimed in claim 1, wherein each of said band shaped conveying members comprises an upper-band shaped conveying member and a lower band-shaped conveying member which cooperated for conveying the sample-supporting thin film.

* * * * *